(12) United States Patent
Sternby et al.

(10) Patent No.: US 7,879,242 B2
(45) Date of Patent: Feb. 1, 2011

(54) METHOD AND DEVICE FOR THE REMOVAL OF PARTIALLY PROTEIN BOUND SUBSTANCES

(75) Inventors: Jan Sternby, Lund (SE); Berit Sternby, Lund (SE)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 12/567,994

(22) Filed: Sep. 28, 2009

(65) Prior Publication Data

US 2010/0044313 A1    Feb. 25, 2010

Related U.S. Application Data

(62) Division of application No. 10/500,478, filed as application No. PCT/SE03/00497 on Mar. 25, 2003, now Pat. No. 7,615,158.

(30) Foreign Application Priority Data

Mar. 27, 2002 (SE) ..................... 0200956
May 2, 2002 (SE) ..................... 0201317

(51) Int. Cl.
  *B01D 61/14* (2006.01)
  *B01D 61/18* (2006.01)
  *B01D 65/02* (2006.01)

(52) U.S. Cl. ............. 210/650; 210/167.01; 210/167.06; 210/175; 210/177; 210/194; 210/195.2; 210/203; 210/252; 210/253; 210/257.2; 210/258; 210/321.6; 210/321.72; 210/323.1; 210/340; 210/428; 210/651; 210/805; 604/4.01; 604/5.04; 604/6.01; 604/6.04; 604/6.09; 604/28

(58) Field of Classification Search .................. 210/636, 210/645, 646, 650, 651, 805, 167.01, 167.06, 210/175, 177, 185, 194, 195.2, 203, 199, 210/252, 253, 257.2, 258, 295, 321.6, 321.69, 210/321.72, 323.1, 340, 428; 604/4.01, 5.04, 604/6.01, 6.04, 6.09, 6.11, 28
See application file for complete search history.

(56) References Cited

U.S. PATENT DOCUMENTS 4,191,182 A    3/1980    Popovich et al.

(Continued)

FOREIGN PATENT DOCUMENTS

EP    0 968 730 A1    1/2000
WO    WO 01/51185 A1    7/2001

OTHER PUBLICATIONS

Gianfranco B. Fiore, et al., "A New Semiemprical Mathematical Model for Prediction of Internal Filtration in Hollow Fiber Hemodialyzers," *Karger, Blood Purif* 2006:24:565-568.

(Continued)

*Primary Examiner*—John Kim
(74) *Attorney, Agent, or Firm*—Finnegan, Henderson, Farabow, Garrett & Dunner, LLOP

(57) ABSTRACT

A method and a device to increase the efficiency of dialysis for the removal from blood of substances that are more or less tightly bound to carriers such as albumin. According to the invention this is accomplished by a simultaneous significant increase of the flow rate of the dialysis fluid and of the area of the membrane that separates the blood from the dialysis fluid, compared to conventional dialysis.

10 Claims, 5 Drawing Sheets

U.S. PATENT DOCUMENTS

| | | |
|---|---|---|
| 4,267,040 A | 5/1981 | Schal |
| 4,435,289 A | 3/1984 | Breslau |
| 4,702,829 A | 10/1987 | Polaschegg et al. |
| 4,711,715 A | 12/1987 | Polaschegg |
| 4,728,496 A | 3/1988 | Petersen et al. |
| 4,784,495 A | 11/1988 | Jonsson et al. |
| 4,861,485 A | 8/1989 | Fecondini |
| 4,906,375 A | 3/1990 | Heilmann |
| 5,626,759 A | 5/1997 | Krantz et al. |
| 5,683,584 A | 11/1997 | Wenthold et al. |
| 5,744,042 A | 4/1998 | Stange et al. |
| 6,039,877 A | 3/2000 | Chevallet et al. |
| 6,117,100 A | 9/2000 | Powers et al. |
| 6,572,641 B2 | 6/2003 | Brugger et al. |
| 6,605,218 B2 | 8/2003 | Kozawa et al. |
| 6,716,356 B2 | 4/2004 | Collins et al. |
| 2005/0131332 A1 | 6/2005 | Kelly et al. |

OTHER PUBLICATIONS

T. Bosch, "Effect of Protein Absorption on Diffusive and Convective Transport Through Polysulfone Membranes," *Contr. Nephrol.*, vol. 46, pp. 14-22 (Karger, Basel 1985).

S. Eloot, et al., "In vitro evaluation of the hydraulic permeability of polysulfone dialysers," *Hydraulic Permeability of Polysulfone Dialysers*, pp. 210-216, (2002).

Leypoldt et al.; "Increases in Mass Transfer-Area Coefficients and Urea Kt/V With Increasing Dialysate Flow Rate Are Greater for High-Flux Dialyzers"; American Journal of Kidney Diseases, vol. 38, No. 3, pp. 575-579, (2001).

METHOD AND DEVICE FOR THE REMOVAL OF PARTIALLY PROTEIN BOUND SUBSTANCES

CROSS-REFERENCE TO RELATED APPLICATIONS

This application is a divisional of U.S. patent application Ser. No. 10/500,478, filed Jan. 28, 2005, now U.S. Pat. No. 7,615,158 which claims the benefit of priority to International Application No. PCT/SE03/00497, filed on Mar. 25, 2003, and of Sweden Application No. 0200956-1, filed on Mar. 27, 2002 and Sweden Application No. 0201317-5, filed on May 2, 2002, Under 35 U.S.C. §119, all of which are incorporated herein by reference.

FIELD OF THE INVENTION

This invention relates to a method and a device for increasing the efficiency of dialysis for the removal of substances from a biological fluid such as blood, which substances are more or less tightly bound to carriers such as albumin.

BACKGROUND

For people who have lost all or most of their kidney or liver functions, it is necessary to find alternative ways of cleaning the blood. One common alternative is dialysis, in which the waste products in the blood are transported across a membrane to a cleaning fluid. In hemodialysis, the most common form of dialysis, blood is removed from the body, and is led to an external device, the dialyzer, which contains a membrane with blood flowing on one side and a dialysis fluid flowing on the other side of the membrane. The blood is then returned to the body. Due to the concentration difference between the blood and the dialysis fluid across the membrane, waste products in the blood will be transported by diffusion to the dialysis fluid. At the same time any excess fluid may be removed by ultrafiltration, which is achieved by creating a pressure difference across the membrane.

This dialysis procedure can be very effective for substances that are dissolved in the body fluids, including the blood plasma. The driving force for the transport across the membrane is the concentration difference, and as long as this concentration difference is maintained, the transport rate can be high. For substances with a zero concentration in the dialysis fluid, the transport rate can be calculated as the product of the blood concentration and a factor known as the dialyzer clearance. The clearance value can be viewed as the fraction of the blood flow that is totally cleared from the substance in question, and is measured in ml/min.

The main determinants for the clearance (Cl) are the flow rates of blood ($Q_b$) and dialysis fluid ($Q_d$), and the transport capacity of the membrane. The membrane can be characterized by its mass transfer coefficient, $k_oA$, which is proportional to the membrane area, and can be interpreted as the clearance that would be obtained at very large flow rates of blood and dialysis fluid. An equation for the dialyzer clearance can be derived theoretically by calculating the concentration profiles along the dialyzer. Considering a mass balance at each point along the dialyzer, taking into account the mass transported by the flows, and the diffusion across the membrane, leads to a set of differential equations for the concentrations along the dialyzer in the direction of the blood flow. The mass removal rate needed for the calculation of clearance is then obtained from the blood flow rate and the calculated change in the blood concentration. In the absence of any ultrafiltration clearance is given by equation 1

$$Cl = Q_b \cdot \frac{(1-e^f) \cdot Q_d}{Q_d - Q_b \cdot e^f} \qquad (1)$$

wherein e denotes the exponential function, and the exponent f is calculated from equation 2

$$f = k_o A \left( \frac{1}{Q_d} - \frac{1}{Q_b} \right) \qquad (2)$$

For the derivation of equations 1 and 2 it is assumed that both blood and dialysis fluid are perfectly mixed at each point along the dialyzer. The concentration is thus assumed to vary along the dialyzer according to the calculated concentration profiles, but the concentrations are assumed to be independent of the distance from the membrane. It is also assumed that the flows are equally distributed in the whole dialyzer. Even with these limitations the equations have been shown in practice to well describe the dependence of clearance on the flow rates of blood and dialysis fluid. These equations, with a correction for ultrafiltration when needed, are therefore often used to describe the capacity of dialyzers.

A closer study of equations 1 and 2 reveals that the clearance can never exceed either of $Q_b$, $Q_d$, or $k_oA$. The dialysis fluid flow rate $Q_d$ and the $k_oA$ are limited only by the available equipment, but the blood flow rate is limited by the rate at which blood can be obtained from the blood access in the patient. This is for dialysis normally in the range 200-500 ml/min. This limits the maximum efficiency that can be obtained in dialysis treatments, and has lead to fairly standardized values for $Q_d$ and membrane $k_oA$ used in normal dialysis treatments, since the cost of higher flow rates and $k_oA$ cannot be justified by a better efficiency.

If $Q_d$ is increased when $Q_b$ and $k_oA$ are fixed, clearance will increase to a certain fraction of the blood flow rate, which is determined by $k_oA$. Already at a $Q_d$ of twice the blood flow rate clearance is close to this limit, and little is gained by going higher. Dialysis fluid flow rates in standard hemodialysis are therefore normally in the range 500-800 ml/min.

If instead $k_oA$ is increased when $Q_d$ and $Q_b$ are fixed, clearance will approach $Q_b$ independently of $Q_d$ (as long as $Q_d$ is higher than $Q_b$). The increase is noticeable even at $k_oA$ values up to 3-4 times the blood flow rate, but for economical and practical reasons dialyzer $k_oA$ values in standard hemodialysis are usually limited to the range 500-1000 ml/min.

The analysis above is valid for substances that are dissolved in fluids such as plasma. But many substances are to a large extent bound to carriers such as albumin. Examples of substances that can bind to albumin are butyric and valeric acid, thyroxine, tryptophane, unconjugated bilirubin, mercaptans, and aromatic amino acids. A number of drugs are known to have a high binding rate to albumin in cases of accidental overdosage or suicidal intoxications by e.g. tricyclic antidepressants, digoxin, digitoxin, theophylline or a benzodiazepine.

Hemoglobin may also act as a carrier, e.g. for carbon monoxide or cyanide. These substances have a high affinity to hemoglobin, and will replace oxygen, which significantly decreases the ability of the blood to transport oxygen.

In many cases it may be important to have a high removal rate also for substances in the blood that to a large extent are bound to proteins or other carriers, such as fungus toxins. But the situation is different from that of the dissolved substances discussed above. Even with a large total amount of partly protein bound and partly dissolved substance in the blood, the plasma concentration may be low, since most of the substance may be bound. The concentration gradient across the membrane will then be small, so that the transport rate in dialysis will be low, as will the treatment efficiency.

Previous attempts to solve this problem have focused on adding a carrier to the dialysis fluid as well. For albumin bound toxins, a common solution is to add albumin to the dialysis fluid. Substances transported across the membrane into the dialysis fluid will then bind to the albumin in the dialysis fluid. This will keep the concentration low in the dialysis fluid, so that the transport across the membrane can continue without a disappearing concentration gradient. The capacity of the dialysis fluid to carry protein bound substances thus becomes much greater, see e.g. U.S. Pat. No. 5,744,042.

With most of the substance bound to carriers, the concentration gradient is still small, and even better results may be achieved if the membrane itself is also modified to enhance the transport. This has been suggested in U.S. Pat. No. 5,744, 042, where the membrane is primed with albumin so that the inner and outer membrane surfaces are covered with albumin, which adheres to the surfaces. Thus, sites are created within the membrane that can act as mediators for the transport across the membrane.

A major disadvantage with adding a carrier like albumin to the dialysis fluid and/or to the membrane is that it is very expensive. It is therefore desirable not to waste this dialysis fluid including albumin. In U.S. Pat. No. 5,744,042 it is suggested to put a cleaning cartridge in the dialysis loop that will remove the bound substances from the carrier to regenerate the dialysis fluid. By doing so only a small amount of dialysis fluid is needed since it can be reused over and over again. The problem is that this fluid will be saturated with all the solutes that are not removed by the cartridge, and it was therefore necessary to introduce a second loop of dialysis in order to clean the primary dialysis fluid, and also to remove any excess fluid that is normally accumulated in a patient between treatments.

SUMMARY OF THE INVENTION

In prior art, the procedure, thus, becomes expensive and slow as well as cumbersome, and there is a need for a simpler way to remove carrier bound substances from blood. The present invention is based on a more careful exploration of the mechanisms behind the transport of carrier bound substances across a dialysis membrane.

A theoretical formula for dialyzer clearance can be derived also in this case, if we assume that the ratio between the total amount of the substance and the amount that is dissolved in plasma is constant. If we denote this ratio by $\alpha$, and define clearance as the removal rate divided by the total concentration in blood (including the fraction that is bound) the formula for clearance becomes modified as shown by equation (3)

$$Cl = Q_b \cdot \frac{(1-e^f) \cdot Q_d/\alpha}{Q_d/\alpha - Q_b \cdot e^f} \quad (3)$$

Compared to equation (2) the exponent f is modified as shown in equation (4)

$$f = \frac{k_o A}{\alpha}\left(\frac{\alpha}{Q_d} - \frac{1}{Q_b}\right) \quad (4)$$

In the derivation of equations 3 and 4 it was assumed that the ratio $\alpha$ is constant over time and in the whole dialyzer. This means that the equilibrium between the carrier bound fraction and the dissolved fraction is assumed to be instantaneous, so that when material is removed by dialysis from plasma, a corresponding amount is immediately released from the carrier. A delay in this process may decrease the resulting clearance, but the decrease can be minimized by various actions to maximize the residence time of the blood in the dialyzer.

The effect of ultrafiltration is also neglected in equations 3 and 4. For dissolved substances ultrafiltration is known to increase clearance by about ⅓ to ½ of the ultrafiltration rate, which usually means an increase of a few percent. For carrier bound substances the effect of ultrafiltration is more complicated. Ultrafiltration in itself does not change the concentration in the remaining blood, and the carrier bound fraction of the substance is therefore unavailable for removal by pure ultrafiltration. Another effect of ultrafiltration is to decrease the flow of plasma, which makes it easier to decrease the plasma concentration of the substance. At the same time the blood becomes more concentrated, so that the concentration of the carrier also increases. This will increase the binding ratio $\alpha$ further, which tends to decrease the removal. The total effect of ultrafiltration on removal of carrier bound substances is probably less than for non bound substances.

The situation becomes different if the ultrafiltration is preceded by dilution of the blood, as is the case in predilution hemofiltration and hemodiafiltration, the latter being a combination of standard hemodialysis and hemofiltration. When the blood is diluted, the concentration of dissolved substance becomes lower, and this causes the carriers to release part of the bound substance. This released substance is then removed by the subsequent ultrafiltration step, which does not change the concentration.

It is possible to calculate the efficiency of such a predilution hemofiltration procedure. The binding ratio $\alpha$ will, however, change when the blood is diluted. For the calculation we instead assume that the amount of substance bound to each carrier molecule is proportional to the concentration of the substance in the surrounding plasma. We also assume that the same flow rate of dialysis fluid $Q_d$ that is added in the dilution step is then removed by ultrafiltration. An analysis of the effect of dilution on the concentrations then shows that clearance in this case is given by equation 5

$$Cl = \frac{Q_d/\alpha}{Q_d/\alpha + Q_b} \cdot Q_b \quad (5)$$

For $\alpha=1$ (no binding) equation 5 agrees with the standard formula for predilution hemofiltration clearance. The effect of binding is to reduce the influence of the dialysis fluid flow rate by a factor of $\alpha$. This flow rate therefore may have to be increased in order to get a sufficient clearance. Since the same flow rate also needs to be removed by ultrafiltration, this increases the demand on the filter to be permeable to the fluid.

The necessary ultrafiltration rate is usually obtained by applying a pressure gradient across the membrane. The ultrafiltration rate is proportional to the applied pressure with a proportionality coefficient denoted $L_pA$, which is proportional to the membrane area. To achieve a sufficient ultrafiltration rate at a moderate pressure it is therefore often necessary to increase the membrane area correspondingly.

Equations 3 and 4 show that in hemodialysis the effect on clearance of the partial binding of the substance to a carrier can be summarized as both membrane mass transfer coefficient $k_oA$ and dialysis fluid flow rate being divided by the binding ratio $\alpha$. Since the value of this ratio $\alpha$ may be 10 or much more, the effect on clearance can be so large that the effect of the dialysis procedure becomes far too small to be of any practical value.

For substances dissolved in plasma it is, as discussed above, normally the blood flow rate $Q_b$ that is the limiting factor for clearance, and it is of limited value to increase $k_oA$ (or $L_pA$ for hemofiltration) or dialysis fluid flow rate $Q_d$. But for carrier bound substances with an a above 3-4, equations 3, 4 and 5 show that it is normally no longer the blood flow rate that is the limiting factor. Instead both $k_oA$ (or $L_pA$ for hemofiltration) and $Q_d$ are limiting and need to be increased. But it does not help much to increase just one of them, since the other one will then still limit the clearance. Instead they both need to be increased simultaneously.

Ideally, both $k_oA$ (or $L_pA$ for hemofiltration) and dialysis fluid flow rate should be increased by a factor of $\alpha$ in order to totally counteract the effect of the binding to the carrier. In cases where the binding factor is large, say up to 100, this would however for practical reasons be difficult to achieve. But usually it is not necessary with such a large increase in clearance, since the carrier is normally present mainly in the blood, and only to much lesser extent in the rest of the body fluids. This means that a large part of the substance is found in the blood, even though the concentration in other body fluids may be the same as in plasma. The apparent total volume of body fluid, i.e. mainly plasma with partially protein bound substances, to be cleaned is therefore usually much smaller than the volume of total body water with therein dissolved non-protein bound substances. Moreover, the total amount of substance (protein bound and dissolved) to be removed is smaller than substances to be removed in normal dialysis, i.e. urea etc.

The dialysis fluid flow rate and the membrane mass transfer coefficient $k_oA$ (or $L_pA$ for hemofiltration) should be increased at least by a factor of 3-4, but preferably by a factor of 10. Even higher factors are useful, but a ten-fold increase may often be sufficient, even for high binding factors above 10 and up to 100. The product of the blood flow rate and the ratio $\alpha$ can be used as a guideline for suitable values of the dialysis fluid flow rate and the membrane mass transfer coefficient $k_oA$ (or $L_pA$ for hemofiltration), but for high binding ratios $\alpha$, 10% of this product may have to suffice.

Since in these cases the blood flow rate often is not the limiting factor, it may even be possible to lower the blood flow rate. The important factor is still to increase the membrane mass transfer coefficient $k_oA$ (or $L_pA$ for hemofiltration) and the dialysis fluid flow rate, and the blood flow rate may then be lowered at least down to a fraction of $1/\alpha$ of the largest of these two. Such an action could limit any detrimental effects on the blood vessels that may be caused by removing large quantities of blood. Thus, patients intoxicated by drugs or other toxins may be treated by the method according to the present invention by inserting needles or catheters in a large but superficial blood vessel such as the Vena Cephalica, where a blood flow rate in the range of 50 ml/min can be obtained.

The lower blood flow rate may also increase the efficiency of the procedure by allowing a longer residence time of the blood in the dialyzer in cases where the equilibrium between the bound and dissolved fractions of the substances has a time delay. The dialysis fluid flow rate and $k_oA$ should still be kept above 2000 ml/min, and preferably above 5000 ml/min or even higher. In hemofiltration $L_pA$ needs to be large enough to allow the necessary ultrafiltration rate with the high dialysis fluid flow rate at a moderate pressure gradient.

The membrane area, which is proportional to $k_oA$ and $L_pA$, can easily be increased either by using several standard dialysis filters in a series or in a parallel configuration, or combinations thereof, or by using specially designed filters with increased membrane area.

To increase the dialysis fluid flow rate requires some further considerations. The production of, say, 5 liters per minute of dialysis fluid puts high demands on the supply of water, which has to be of a high quality.

The dialysis fluid also has to contain electrolytes like Sodium, Potassium, Calcium, Chloride and Bicarbonate in concentrations that correspond to those of blood. This is in normal dialysis achieved by mixing the water with concentrated solutions of these ions. With the large amount of fluid required for the present invention the required amount of concentrate will also be large. The handling of these large quantities could be significantly simplified if one or more of the electrolytes are supplied in dry form as suggested in U.S. Pat. No. 4,784,495. Another method to handle this problem is to use a large central mixing station to prepare the dialysis fluid, which is then pumped through delivery lines to the place of use.

One way to decrease the large demand for water and concentrates is to regenerate the spent dialysis fluid by an ultrafiltration process. A filter with a high permeability for water, and with a suitable pore size to allow the electrolytes to pass, but not the substances that are to be removed, is placed in the spent dialysis fluid. The ultrafiltrate is reused, and the now concentrated spent dialysis fluid is wasted. This process is possible to use in cases where the substances to be removed are sufficiently larger than the electrolytes.

Furthermore, the dialysis fluid has to have a temperature that is close to normal body temperature. The dialyzer will act as a heat exchanger between blood and the dialysis fluid. If the dialysis fluid is cold the blood that is returned to the patient will have a too low temperature, which will cause discomfort. In normal dialysis treatments all of the dialysis fluid is heated to around 38° C. The power required for heating a dialysis flow rate of 500-800 ml/min is at the limit of what a standard wall outlet can produce. For the higher end of the flow rates it may not even be sufficient, especially if the incoming water is particularly cold. In such cases a heat exchanger is often used to transfer heat from the spent dialysis fluid to the incoming water.

For the present invention there is needed a dialysis flow rate that may be 10 times higher than normal. Even a heat exchanger is then not sufficient to allow the total amount of dialysis fluid to be sufficiently heated by the power available in a standard wall power outlet. Performing the main part of the procedure using unheated dialysis fluid can solve this problem. The blood can then be heated just before it is returned. This can be done e.g. using a blood heater that acts on the outside of the blood line.

Another possibility is to heat a small fraction of the total amount of dialysis fluid. The system should then be arranged so that the unheated portion of the dialysis fluid is used first, and the final heated fraction of the dialysis fluid is used for the final treatment of the blood just before it is returned to the patient.

The use of unheated dialysis fluid for the major part of the procedure, and the consequent lowering of the blood temperature, might affect the efficiency. It is well known that the effect of diffusion decreases when the temperature is decreased, but temperature may also affect the binding ratio α. Various carrier/toxin combinations may react differently in this respect. The efficiency of the procedure will decrease if α increases.

An alternative method to handle the heating problem is to use a central mixing station for, both the preparation and heating of the dialysis fluid. The whole procedure may then be performed at an elevated temperature in cases where this may be important for efficiency reasons. Warm dialysis fluid with the correct composition of water and electrolytes is then distributed from a central mixing station to each of the sites where the dialysis machines are situated.

In order to achieve the effect of a larger clearance of carrier bound substances it is necessary to address both issues of membrane area and flow of dialysis fluid. As disclosed in the present invention this can be done by making both membrane area and dialysis fluid flow rate large. In U.S. Pat. No. 5,744, 042 both factors are instead handled by adding the carrier albumin. These two approaches could also be combined. A carrier, such as albumin, could be added to the dialysis fluid, but not to the membrane, which instead is made large as described above. Alternatively, the membrane is primed with albumin, but no carrier is added to the dialysis fluid, which instead is supplied in a large amount.

In a further embodiment of the present invention a carrier such as albumin is added to the large dialysis fluid flow and the large membrane is primed with the same or other carrier. The carrier is e.g. serum albumin. The concentration of serum albumin is preferably above 10 g/l. This embodiment of the invention is advantageous where very strongly bound substances are to be removed or where a ratio between bound and dissolved substances is exceptionally high.

In still a further embodiment of the invention a large dialysis fluid flow rate of about 4000 ml/min could be combined with a large membrane having a $k_oA$ of about 4000 ml/min and a concentration of a carrier such as serum albumin which is about 5 g/l. This embodiment is advantageous as the concentration of expensive albumin is limited while the effect of the dialysis treatment is kept on an acceptable level.

DETAILED DESCRIPTION OF EMBODIMENTS OF THE INVENTION

Figure 1:
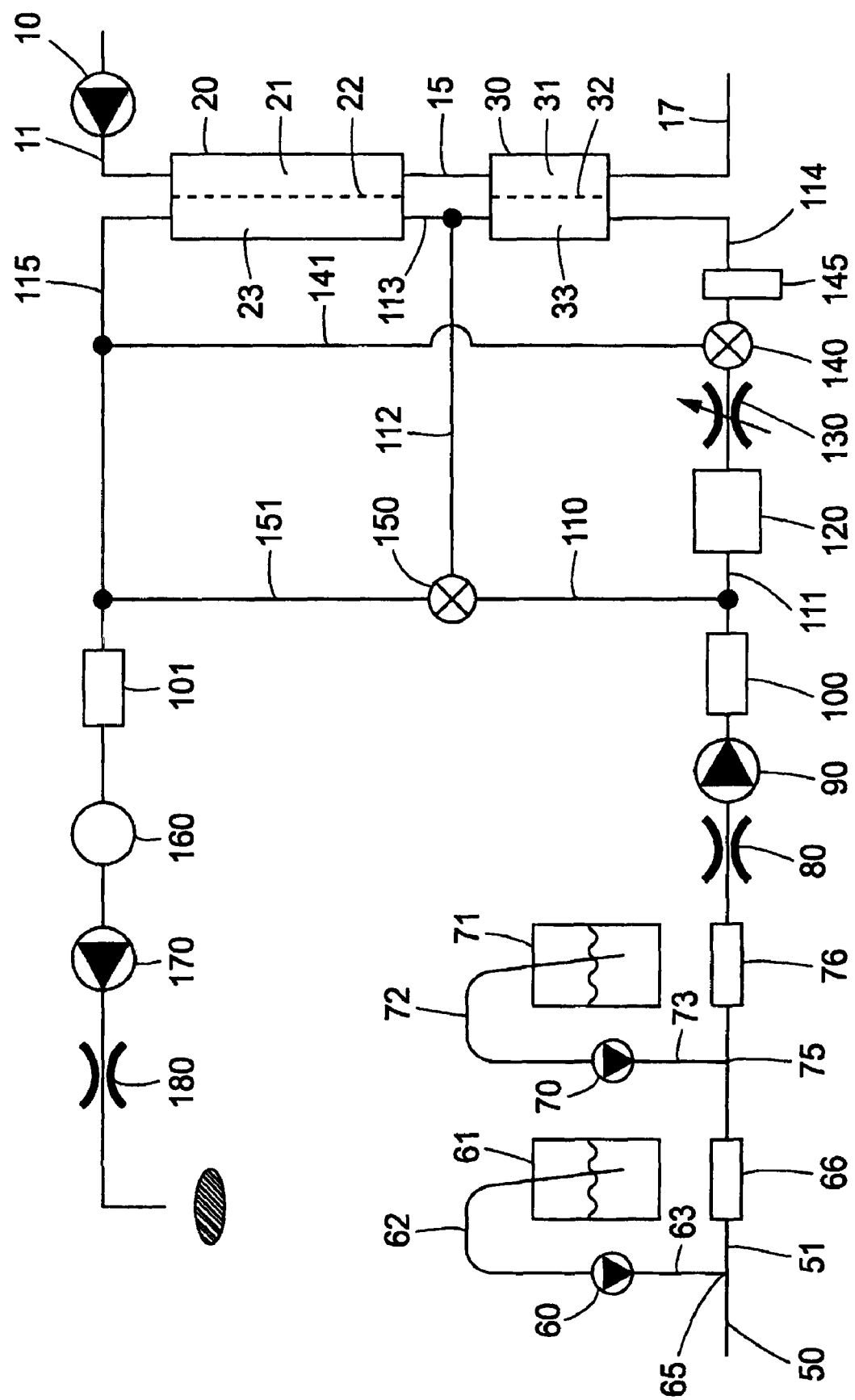
FIG. 1 is a block diagram, which schematically shows a dialysis system to carry out the invention.

A first embodiment of the invention is shown in FIG. 1, which schematically shows a system with a close resemblance to a standard system for hemodialysis. Blood is transported with the help of a pump 10 from the patient via an arterial blood line 11 through the blood compartment 21 of a large dialyzer 20, and then via blood line 15 into the blood compartment 31 of a smaller dialyzer 30. It is then returned to the patient via blood line 17. Semipermeable membranes 22 and 32 in dialyzers 20 and 30, respectively, separate the blood compartments 21 and 31, respectively, from the dialysate compartments 23 and 33, respectively.

The pore size of the semipermeable membranes 22 and 32 should be chosen large enough to allow the passage of the toxins that are to be removed, the size of which in some cases are several thousand Daltons. The membranes should, on the other hand, effectively prevent the passage of carriers such as albumin, which has a size of about 66000 Daltons. These requirements can be fulfilled by membranes made from e.g. polysulfones, polyamides, polycarbonates, polyesters, acrylonitrile polymers, vinyl alcohol polymers, acrylate polymers, methacrylate polymers or cellulose acetate polymers.

For the preparation of a dialysis fluid, clean water obtained from a clean water plant conventionally used in dialysis treatments enters the water inlet 50, and is then mixed to the correct composition in two steps. In the first step a concentrate pump 60 delivers a concentrated solution of Chlorides of Sodium, Potassium, Calcium and Magnesium together with an acid, such as Acetic acid, Hydrochloric acid or Citric acid, from a container 61 via concentrate lines 62 and 63 to a mixing point 65 in the main fluid line 51. The conductivity of the mixture is measured in a conductivity cell 66. The measured conductivity is registered in a control unit (not shown), and is compared to the desired value. The control unit controls the speed of the concentrate pump 60 so that the conductivity is kept at the desired value.

In the second mixing step a concentrate pump 70 delivers a concentrated solution of Sodium Bicarbonate from a container 71 via concentrate lines 72 and 73 to a mixing point 75 in the main fluid line 51. The conductivity of the mixture is measured in a conductivity cell 76. The measured conductivity is registered in the control unit (not shown), and is compared to the desired value. The control unit controls the speed of the concentrate pump 70 so that the total conductivity is kept at the desired value.

The dialysate flow then passes a restrictor 80, with the flow rate maintained by a pump 90 in the main fluid line. The effect of the restrictor 80 is to allow a sufficiently low dialysate pressure in the dialyzers, so that a sufficient amount of fluid can be retracted from the blood by the process of ultrafiltration through the semipermeable membranes 22 and 32, irrespectively of the pressure on the blood side. The flow rate is measured in a flow cell 100, and the measured value is registered in a control unit (not shown) that will control the speed of pump 90 so that the desired fluid flow rate is achieved.

The main fraction of the flow is then directed through line 110 for further transport via valve 150 and lines 112 and 113 directly to the dialysate compartment 23 of the large dialyzer 20. The rest of the flow is directed through line 111 to a heater 120, an adjustable restrictor 130 and a flow meter 145. The heater 120 will heat the fluid to some temperature below 40° C. as measured by a not shown temperature sensor. This temperature is chosen to give the blood that leaves dialyzer 30 a suitable temperature. The adjustable restrictor 130 is designed to assure that only about 500 ml/min of the flow, as measured by the flow meter 145, passes this way, and may be adjustable to allow for this part of the flow to stay the same even though the main flow may be different at different occasions. If the temperature and the composition of the flow are correct the three way valve 140 may be set to allow the flow to continue through line 114 to the dialysate compartment 33 of the smaller dialyzer 30. After passing dialyzer 30 this flow will continue through line 113 where it will meet the main fraction of the flow, and all of the flow will pass dialyzer 20 and continue through line 115.

If the dialysis fluid does not fulfill the requirements, e.g. on temperature or composition, or if for some other reason no dialysate flow is wanted in the dialyzers, the control unit will set the three way valves 140 and 150 to direct the fluid through bypass lines 141 and 151, respectively, and the direct lines 112 and 114 respectively will be closed off. All of the dialysate fluid will then go directly to line 115 without passing the dialyzers, and this will guarantee that any blood in the dialyzers cannot be damaged by dialysis fluid that does not have the correct composition or temperature.

The spent dialysis fluid is then led to a second flow cell 101, where the flow rate is measured and is registered by the control unit. The difference of the accumulated flows registered in flow cells 100 and 101 will be a measure of the volume that has been ultrafiltered from the blood. The control unit will adjust this volume to a desired value by controlling the speed of pump 170, which controls the flow rate of the spent dialysate. The effect of the restrictor 180 is to allow positive pressures in the dialysate compartments 23 and 33 in order to limit the ultrafiltration in cases where the pressure on the blood side is high. Also shown is a blood leak detector 160 designed to detect also small leakages of blood into the dialysis fluid. Should this occur, the blood leak detector will send a signal to the control unit, which will activate the three way valves 140 and 150 so that the dialysis fluid bypasses the dialyzers, and the blood pump 10 is stopped. Other actions may also be initiated, such as emitting an alarm signal.

Only parts that are relevant to the present invention have been included in the description above. Several other features may be necessary for a successful operation of the system, but are well known from standard dialysis machines. Such well known features include, but are not limited to, degassing of the dialysis fluid before the dialyzers, double measurements of a number of essential parameters to obtain double safety, measurement of the pH of the dialysis fluid, clamps on the blood lines that make it possible to seal off the dialyzers from the rest of the blood lines, and a drip chamber with an air detector in the venous blood line 17.

To a large degree the system is set up and controlled much like a standard system for hemodialysis. The small dialyzer 30 may be a standard filter for hemodialysis, but the large dialyzer 20 shown in FIG. 1 is much larger. Depending on the substances that are to be removed it may have a membrane area in the range 8-10 m$^2$ or larger, resulting in a k$_o$A value of 4000 ml/min or larger. For substances that are tightly bound to their carriers, i.e. substances with a large value of α, the k$_o$A value needs to be large. The upper limit is set mainly by practical and economical limitations.

At startup, the blood lines are supplied with a priming solution, such as physiological saline solution, and the control unit performs a number of safety tests before the correct settings are put into effect for the conductivities, the temperature in the heater and the dialysis fluid flow rates.

According to the invention the main flow rate of the dialysis fluid has to be much larger than for normal hemodialysis. Depending on the substances that are to be removed it should be 2 l/min or higher, preferably 5 l/min or higher, but with no upper limit other than dictated by practical and economical circumstances. The chosen main flow rate is transferred to the control unit, which will then control the pump 90 so that flow cell 100 measures this value. The restrictor 130 may then have to be adjusted so that the heated flow rate as shown by flow meter 145 is close to 500 ml/min.

When all tests have been performed and all parameters are controlled to their correct values blood is introduced into the blood line 11, and the three way valves 140 and 150 are set to allow the dialysis fluid to pass through the dialyzers 20 and 30. The dialysis is continued until the required amount of the substance has been removed. The time required will depend on the parameters of the dialysis and the binding ratio α. If it is possible to obtain a high blood flow rate, so that a high clearance of a few hundred ml/min can be reached, it may be possible to remove up to 90% of a substance with a in the range 5-10 in 30-60 minutes because of the efficient removal rate. This may be important in cases of acute poisoning. In other cases, where the binding ratio α is much higher, and a high blood flow rate does not help, the treatment may have to continue for several hours or up to a day.

Figure 2:
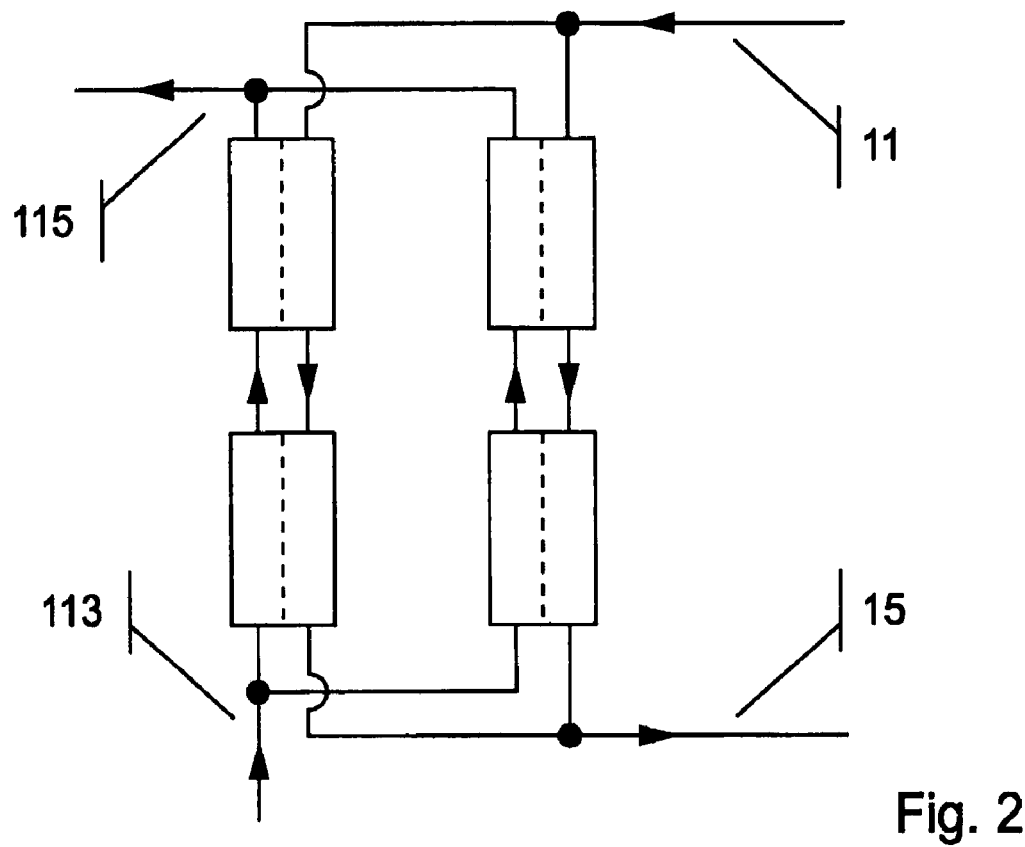
FIG. 2 is a block diagram showing an alternative arrangement of dialyzers.

In an alternative embodiment, the large dialyzer 20 is replaced by a number of smaller dialyzers, which may each be a standard filter for hemodialysis. FIG. 2 shows a configuration with two arms in parallel, each with two dialyzers in series, both on the blood side and on the dialysis fluid side. The incoming blood line 11 is split up into two lines, each of which goes into one arm with two dialyzers in series. The two blood lines coming out from the two arms are then joined again in blood line 15, which leads to the small dialyzer 30. In a corresponding manner, the fluid line 113 is split up into two lines, each of which goes into one of the two arms with two dialyzers in series. All of the spent dialysis fluid is then collected in line 115.

Figure 3:
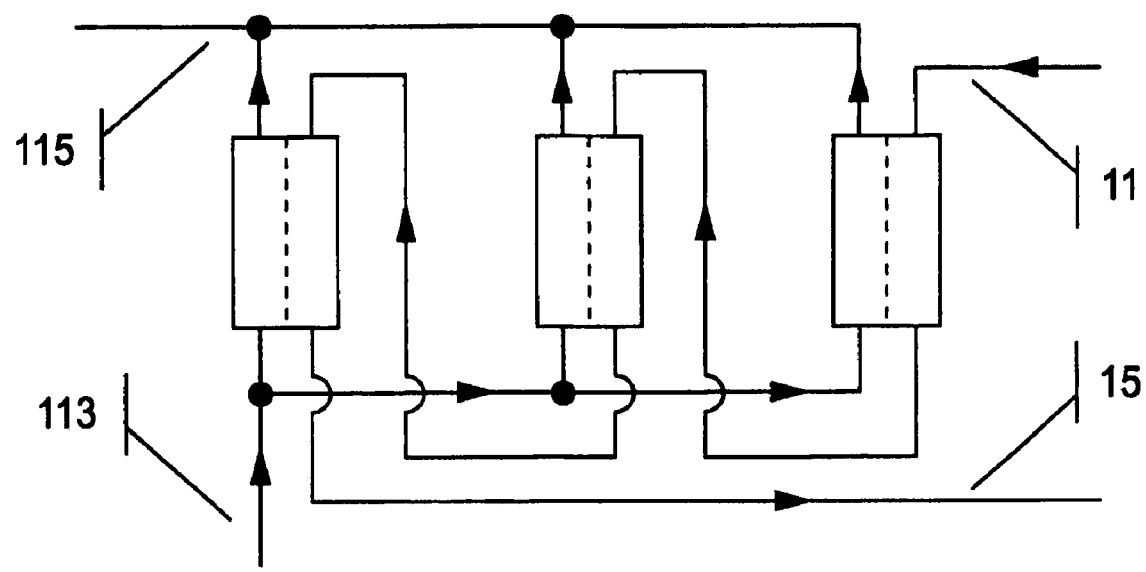
FIG. 3 is a block diagram showing yet another arrangement of dialyzers.

Any number of dialyzers, and any combination of series and parallel configurations is possible. The configurations need not even be the same on the blood side and the dialysis fluid side. For example, the blood side of all dialyzers may be arranged in series, while the dialysis fluid side may be arranged in parallel, as shown in FIG. 3 with 3 dialyzers. The series configuration has the disadvantage of creating a higher pressure drop, whereas in the parallel configuration the flow rate will be lower, which may give a decreased performance due to insufficient filling of the dialyzers. A combination of series and parallel arrangement, as shown in FIG. 2, is therefore preferred.

Figure 4:
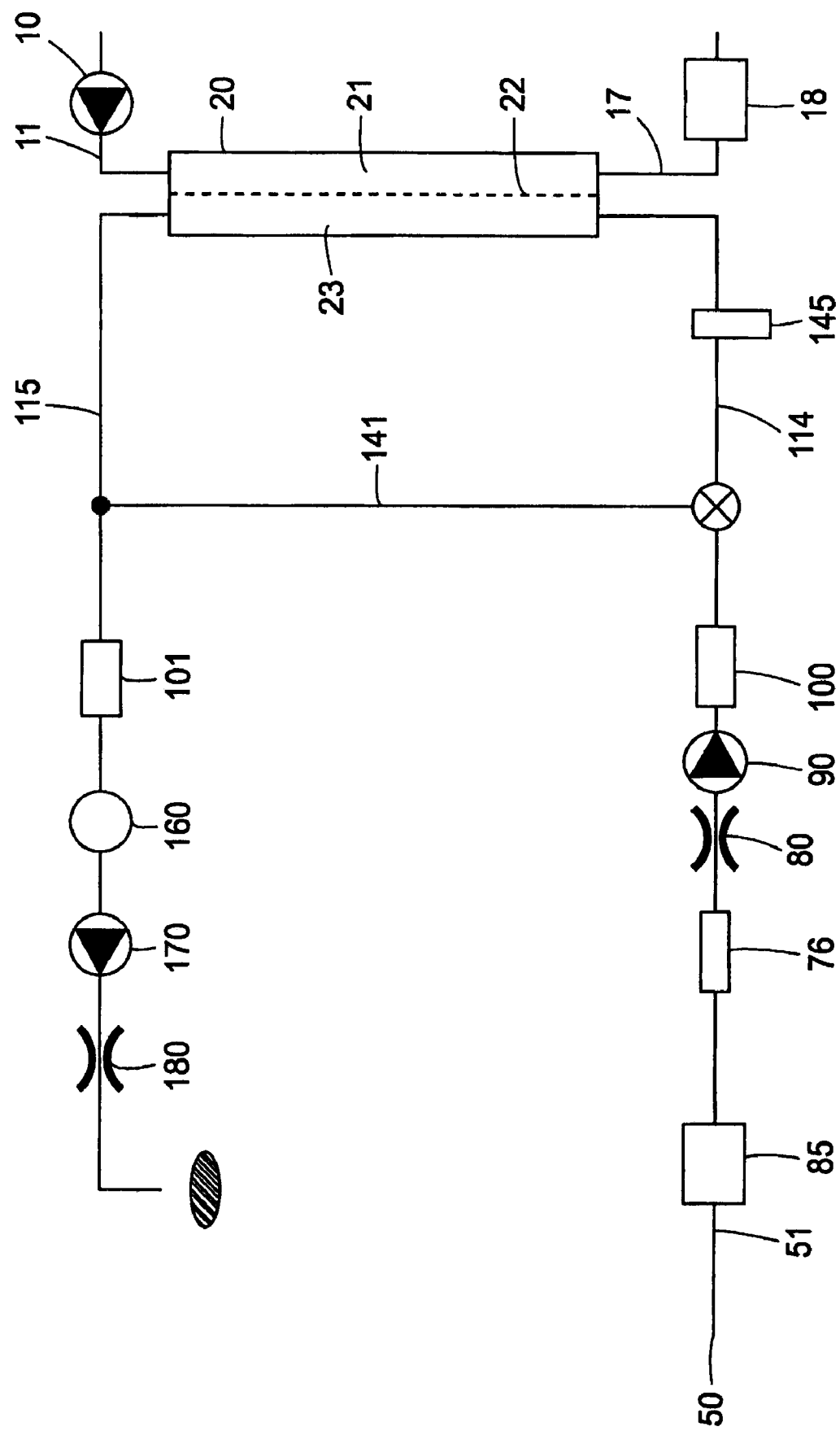
FIG. 4 is a block diagram, which schematically shows an alternative dialysis system to carry out the invention.

In yet another embodiment shown in FIG. 4 the dialysis fluid comes to the system ready to use from a central mixing system. Since all of the dialysis fluid may then already be at almost the correct temperature there is no need to separate the dialysis fluid into a cold part and a heated part, and it is possible to use only one large dialyser. Similar to FIG. 1 blood is transported with the help of a pump 10 via an arterial blood line 11 through the blood compartment 21 of a large dialyzer 20 and is then returned via blood line 17. An optional blood heater 18 may be attached to blood line 17 to heat the blood before it is returned. Such a heater may e.g. transfer heat to the outside of a blood line that is wound around the heater, and may have a capacity to perform all the heating of the blood that is necessary. This would allow the use of dialysis fluid that has not been heated, and heater 85 could then be omitted. The semipermeable membrane 22 in the dialyzer 20 separates the blood compartment 21 from the dialysate compartment 23.

The fluid enters the system at the fluid inlet 50 and is transported through line 51 to a heater 85. Even though the fluid should have almost the desired temperature when it enters the system, there may be a need for a final small adjustment. The composition of the fluid as reflected in its conductivity is checked in the conductivity cell 76. The function of restrictor 80, pump 90 and flow cell 100 is the same as in FIG. 1, i.e. to allow a sufficiently low pressure in the dialysis fluid compartment for an adequate ultrafiltration to take place, and to measure and maintain the flow rate at a desired level.

The flow is then under normal conditions directed through the three way valve 140 and line 114, past the flow meter 145 to the dialysis fluid compartment 23 of the dialyzer 20, which it leaves through line 115. In case some problems occurs that might lead to unwanted effects on the blood in the dialyzer, a control unit (not shown) will set the three way valve to bypass the fluid through line 141 instead of through the dialyzer.

The spent dialysis fluid is then led to a second flow cell 101, where the flow rate is measured and is registered by the control unit. The difference of the accumulated flows registered in flow cells 100 and 101 will be a measure of the volume that has been ultrafiltered from the blood. The control unit will adjust this volume to a desired value by controlling the speed of pump 170, which controls the flow rate of the spent dialysate. The effect of the restrictor 180 is to allow a positive pressure in the dialysate compartment 23 in order to limit the ultrafiltration in cases where the pressure on the blood side is high. Also shown is a blood leak detector 160 designed to detect also small leakages of blood into the dialysis fluid. Should this occur, the blood leak detector will send a signal to the control unit, which will activate the three way valve 140 so that the dialysis fluid bypasses the dialyzer, and the blood pump 10 is stopped.

Again, only parts that are relevant to the current invention have been included in the description above. Several other features, e.g. those listed in connection with FIG. 1, may be necessary for a successful operation of the system, but are well known from standard dialysis machines. Variations and combinations of features described above are also possible. Instead of one large dialyzer as shown in FIG. 4 it is possible to use various combinations of smaller, standard dialyzers as shown in FIG. 2 and FIG. 3.

In a different embodiment of the invention, also shown in FIG. 4, the same large flow of dialysis fluid is used as discussed above, but the membrane 22 of the filter 20 has been coated with albumin in a pretreatment as disclosed in U.S. Pat. No. 5,744,042. The flow rate of dialysis fluid needs to be above 2 l/min, preferably above 5 l/min, and at least 10 times the blood flow rate, but with such a membrane coating the membrane area no longer needs to be large. The coating of the membrane can be done long before the use of the filter, which can then, under suitable conditions, be stored for many months. Another method is to use a standard synthetic membrane, such as a polyamide or polysulfone 18 membrane, which, just before starting the treatment, is primed with a saline solution containing albumin in a concentration above 10 g/l, or preferably above 40 g/l and more preferably above 70 g/l. Priming is performed by directing the solution past one or both sides of the membrane with the help of the pumps in the system.

The dialysis fluid in FIG. 4 is delivered from a central mixing station. Alternatively it can also in this embodiment be prepared locally as shown in FIG. 1.

Figure 5:
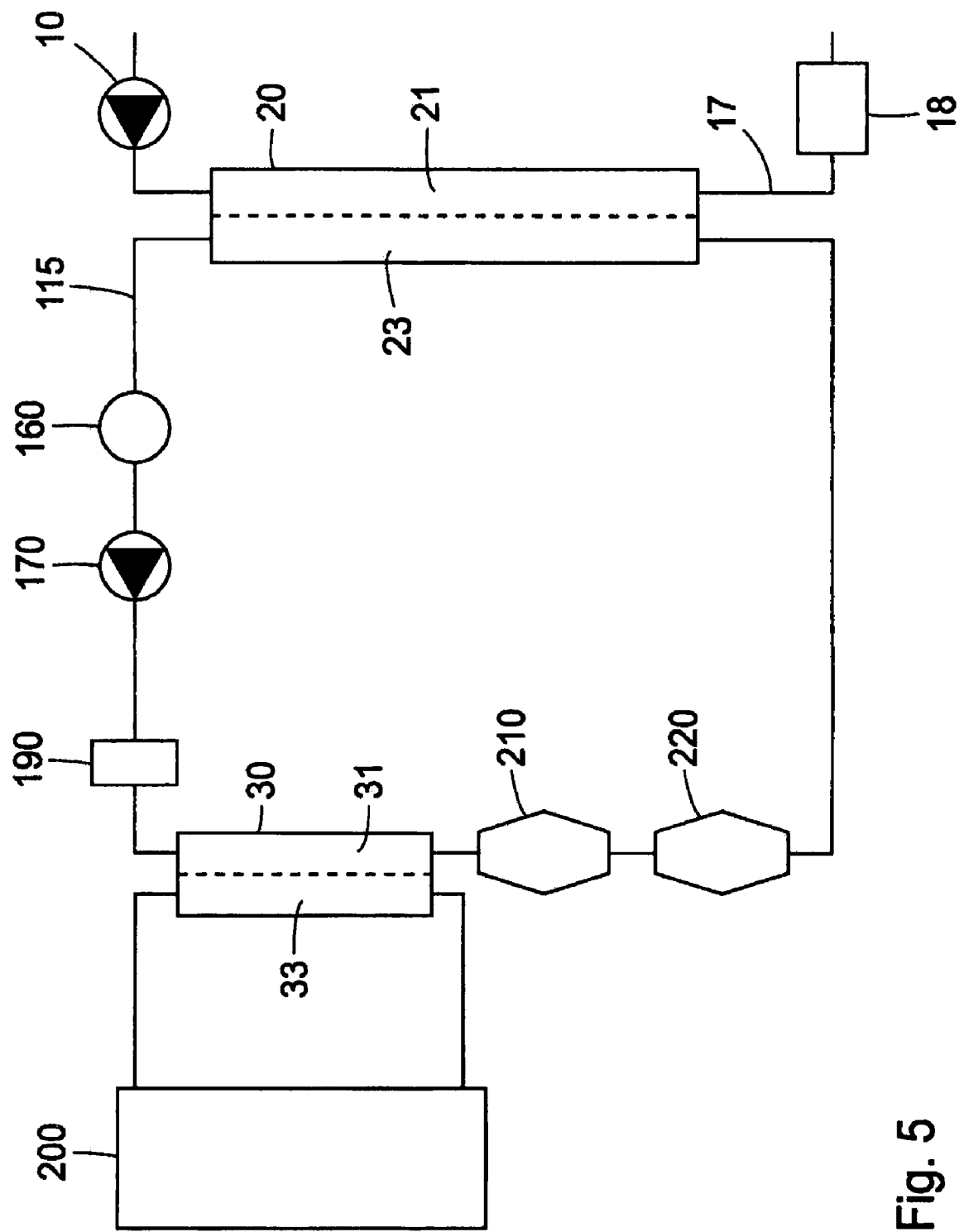
FIG. 5 is a block diagram, which schematically shows yet another dialysis system to carry out the invention.

FIG. 5 shows an embodiment where a dialyzer 20 with the same large surface area as discussed above is used, but the carrier albumin is added to the dialysis fluid. The concentration of albumin should be above 10 g/l, preferably above 40 g/l and more preferably above 70 g/l. The addition of albumin to the dialysis fluid increases its transport capacity of protein bound substances so that it is no longer necessary to increase the flow rate above conventionally used flow rates of 500-1 000 ml/min. To counteract completely the effect of protein binding, the membrane area in dialyzer 20 should preferably be increased by a factor a above what would normally be used. In practice, this may be impractical or too costly to achieve, and smaller areas may have to suffice. In any case, $k_oA$ needs to be at least 5 times the blood flow rate, preferably 10 times the blood flow rate, or above 2000 ml/min, preferably above 4000 ml/min, for the membrane to have an acceptable transport capacity.

In order to minimize the consumption of albumin, the albumin containing dialysis fluid is circulated in a closed loop in the embodiment shown in FIG. 5. Blood pump 10 delivers blood from the patient into the blood compartment 21 of the large dialyzer 20, and the blood is returned to the patient via line 17 and an optional blood warmer 18.

The albumin containing dialysis fluid is circulated through the dialysate compartment 23 by pump 170. A blood leak detector 160 and a bubble separator 190 are also placed in line 115. The dialysis fluid then passes the blood compartment 31 of a second dialyzer 30, which is of conventional type. By connecting the dialysate side 33 to a conventional dialysis machine 200 this dialyzer will remove water and waste products like urea and creatinine that are dissolved in the dialysis fluid. The dialysis fluid then passes two adsorption columns 210 and 220 before it is returned to dialyzer 20.

Columns 210 and 220 contain material with a high affinity for the protein bound substances that are bound to albumin in the dialysis fluid. These substances will therefore be trapped in the columns, and the albumin in the dialysis fluid is again free to act as carrier to new molecules in dialyzer 20. Columns 210 and 220 may e.g. be charcoal adsorbent columns like the Adsorba 300 C from Gambro AB or N350 from Asahi, and/or an anion exchange column like BR350 from Asahi. The number of columns required and their types may depend on the substance or substances that are to be removed.

In cases e.g. poisoning where no removal of completely dissolved waste products and water is required, i.e. only protein bound substances need to be removed, dialyzer 30 and dialysis machine 200 are not needed, and can be left out. Also, the columns 210 and 220 may be left out if the amount of albumin present in the dialysis loop is sufficient to carry the total amount of protein bound substances that is to be removed. Various configurations can thus be conceived within the scope of this embodiment.

Alternatively the embodiment shown in FIG. 5 comprises a large surface area dialyser 20 of the same type as disclosed in FIG. 4 that is coated with a carrier, e.g. albumin.

Figure 6:
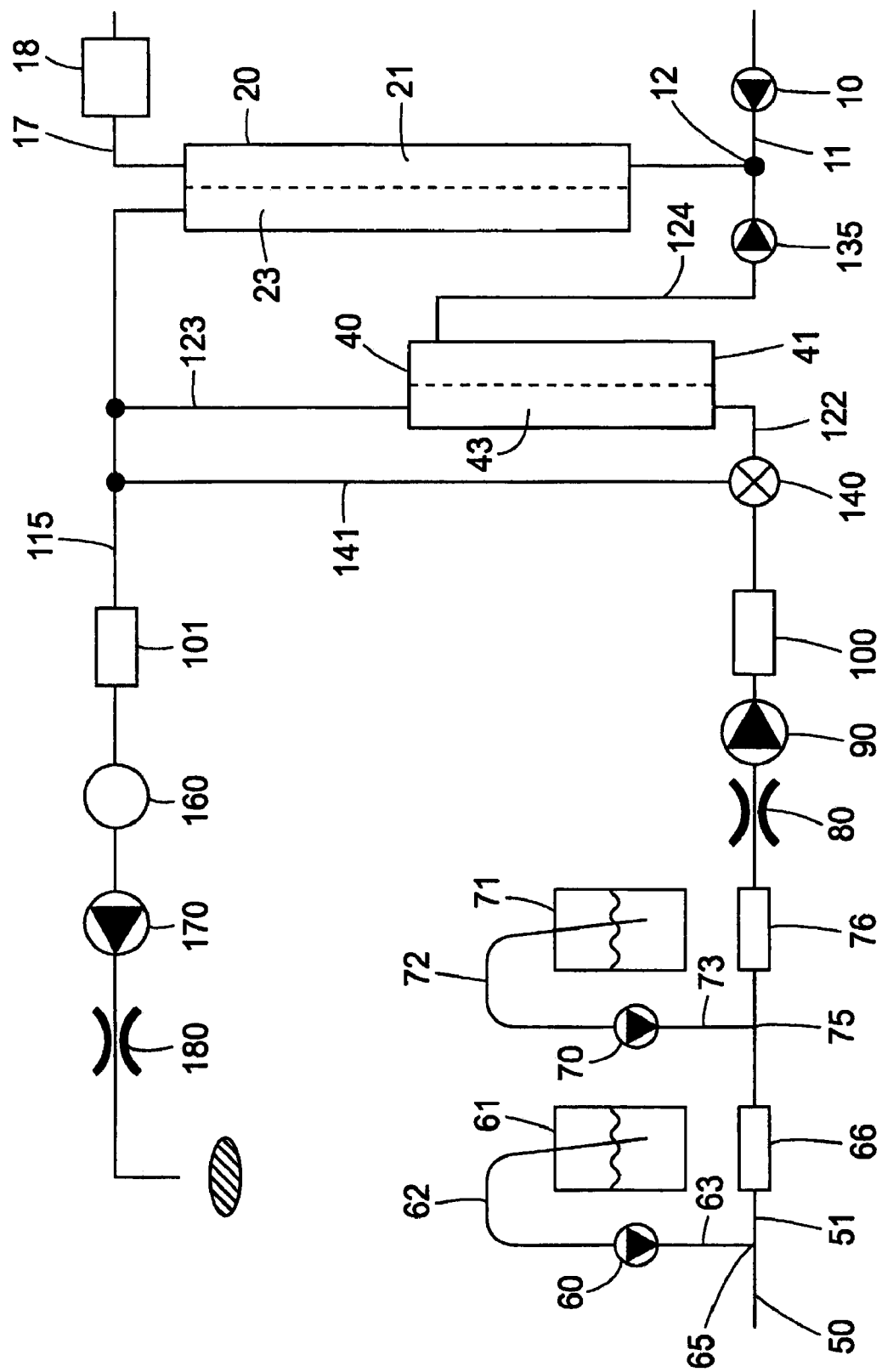
FIG. 6 is a block diagram, which schematically shows a predilution hemofiltration system to carry out the invention.

The embodiment shown in FIG. 6 is adapted to carry out the invention using predilution hemofiltration, which is performed with blood and dialysate in a cocurrent configuration, i.e. the blood and the ultrafiltered dialysate flow in the same direction in the dialyzer. Similar to FIG. 4 blood is transported with the help of a pump 10 via an arterial blood line 11 through the blood compartment 21 of a large dialyzer 20 and is then returned via blood line 17. A blood heater 18 may be attached to blood line 17 to heat the blood before it is returned.

The dialysis fluid enters the system at 50, and is treated exactly as in FIG. 1 until it leaves the flow cell 100. The flow is then under normal conditions directed through the three way valve 140 and line 122 to compartment 43 of the ultrafilter 40. In case some problems occurs that might lead to unwanted effects on the blood in the dialyzer, a control unit (not shown) will set the three way valve to bypass the fluid through line 141 instead of through the ultrafilter.

A pump 135 will be adjusted by a control unit (not shown) to deliver the exact flow of dialysis fluid required from compartment 41 of the ultrafilter, through line 124 to mixing point 12, where the dialysis fluid and the blood are mixed before entering dialyzer 20. Any unused dialysis fluid will leave compartment 43 through line 123, and this fluid together with the ultrafiltrate from compartment 23 of dialyzer 20 will be directed through line 115, flow cell 101, blood leak detector 160 and restrictor 180 by pump 170. The control of this part of the system is identical to that of FIG. 1.

The embodiments shown above are only examples of how the invention could be carried out, and other embodiments are possible for large or small parts of the system. The large quantities of dialysis fluid needed will e.g. require large quantities of electrolyte concentrates supplied in the containers 70 and 71 of FIG. 1. The handling of these large quantities could be significantly simplified if one or more of the electrolytes are supplied in dry form as suggested in U.S. Pat. No. 4,784,495. Also, for the control of ultrafiltration, the use of pump 170 and flow cells 100 and 101 could be replaced by a system with balancing chambers and a separate ultrafiltration pump as described in U.S. Pat. No. 4,267,040 or similar. In FIG. 4, the dialysis fluid does not have to be preheated, and heater 85 is not needed, if the blood before being returned is instead heated by a blood warmer attached directly to line 17. This principle can of course also be applied if the dialysis fluid is prepared in the machine as shown in FIG. 1, and there is then no need to split the fluid into a heated and a non heated part. In FIG. 6 it would e.g. be possible to use centrally prepared dialysis fluid as in FIG. 4, several smaller dialyzers similar to FIGS. 2 and 3, or a final dialyzer instead of heater 18 for the heating of the blood.

The invention claimed is:

1. A method for removing partially carrier bound substances from blood comprising a blood circuit, a fluid circuit, and a filter having a semipermeable membrane separating a fluid compartment from a blood compartment, where blood is directed through the blood compartment and a cleaning fluid is directed through the fluid compartment wherein:
    a mass transfer coefficient $k_oA$ of the filter is at least 2000 ml/min;
    a ratio between the mass transfer coefficient $k_oA$ of the filter and a blood flow rate is at least 5;
    a cleaning fluid flow rate is at least 2000 ml/min; and
    a ratio between the cleaning fluid flow rate and the blood flow rate is at least 5.

2. A method according to claim 1, wherein
    the ratio between the mass transfer coefficient $k_oA$ of the filter and the blood flow rate is at least 10; and
    the ratio between the cleaning fluid flow rate and the blood flow rate is at least 10.

3. A method according to claim 1, wherein
    the mass transfer coefficient $k_oA$ of the filter is at least 5000 ml/min; and
    the cleaning fluid flow rate is at least 5000 ml/min.

4. A method according to claim 1, wherein, parameters are chosen in relation to the product of a blood flow rate $Q_b$ and a factor $\alpha$ denoting the total amount of substance to be removed in relation to the fraction dissolved in plasma,
    the mass transfer coefficient $k_oA$ of the filter is at least 10% of said product; and
    the cleaning fluid flow rate is at least 10% of said product.

5. A method according to claim 4, wherein
    the mass transfer coefficient $k_oA$ of the filter is at least 100% of said product; and/or
    the cleaning fluid flow rate is at least 100% of said product.

6. A device configured to remove partially carrier bound substances from blood comprising a blood circuit, a fluid circuit, and a filter having a semipermeable membrane separating a fluid compartment from a blood compartment, where blood is directed through the blood compartment and a cleaning fluid is directed through the fluid compartment wherein:
    a mass transfer coefficient $k_oA$ of the filter is at least 2000 ml/min;
    a ratio between the mass transfer coefficient $k_oA$ of the filter and a blood flow rate is at least 5;
    a cleaning fluid flow rate is at least 2000 ml/min; and
    a ratio between the cleaning fluid flow rate and the blood flow rate is at least 5.

7. A device according to claim 6, wherein
    the ratio between the mass transfer coefficient $k_oA$ of the filter and the blood flow rate is at least 10; and
    the ratio between the cleaning fluid flow rate and the blood flow rate is at least 10.

8. A device according to claim 6, wherein
    the mass transfer coefficient $k_oA$ of the filter is at least 5000 ml/min; and
    the cleaning fluid flow rate is at least 5000 ml/min.

9. A device according to claim 6, wherein parameters are chosen in relation to the product of a blood flow rate $Q_b$ and a factor $\alpha$ denoting the total amount of substance to be removed in relation to the fraction dissolved in plasma,
    the mass transfer coefficient $k_oA$ of the filter is at least 10% of said product; and
    the cleaning fluid flow rate is at least 10% of said product.

10. A device according to claim 9, wherein
    the mass transfer coefficient $k_oA$ of the filter is at least 100% of said product; and/or
    the cleaning fluid flow rate is at least 100% of said product.

* * * * *